United States Patent
Reyes et al.

(10) Patent No.: US 10,123,847 B2
(45) Date of Patent: Nov. 13, 2018

(54) SURGICAL DEVICE HAVING MULTIPLE RECEPTACLES

(75) Inventors: Rogelio Reyes, El Paso, TX (US); Douglas Robards, Gurnee, IL (US); Alejandro Puentes, El Paso, TX (US)

(73) Assignee: ALLEGIANCE CORPORATION, Wauekgan, IL (US)

( * ) Notice: Subject to any disclaimer, the term of this patent is extended or adjusted under 35 U.S.C. 154(b) by 243 days.

(21) Appl. No.: 13/007,240

(22) Filed: Jan. 14, 2011

(65) Prior Publication Data

US 2011/0174318 A1 Jul. 21, 2011

Related U.S. Application Data

(60) Provisional application No. 61/295,531, filed on Jan. 15, 2010.

(51) Int. Cl.
| | |
|---|---|
| *A61B 19/10* | (2006.01) |
| *A61B 46/23* | (2016.01) |
| *A61B 50/20* | (2016.01) |
| *A61B 50/30* | (2016.01) |
| *A61B 46/00* | (2016.01) |

(52) U.S. Cl.
CPC ............. *A61B 46/23* (2016.02); *A61B 46/00* (2016.02); *A61B 50/20* (2016.02); *A61B 50/30* (2016.02); *A61B 2046/234* (2016.02); *A61B 2046/236* (2016.02); *A61B 2050/3008* (2016.02)

(58) Field of Classification Search
CPC ....... A61B 19/00; A61B 19/08; A61B 19/081; A61B 19/082; A61B 19/086; A61B 19/088; A61B 19/10; A61B 2019/103; A61B 2019/106; A61B 46/00; A61B 46/20; A61B 46/23; A61B 46/40; A61B 2046/234; A61B 2046/236; A61B 50/20; A61B 50/30; A61B 2050/3008; A61B 2050/3009; A61B 2050/3014; A61B 2050/3015

USPC ............ 128/846, 849, 852–854; 200/592.01, 200/495.01–495.11, 23.2, 23.6, 23.8, 200/23.83, 23.87, 23.88, 23.89, 23.9, 200/23.91, 500, 200, 203.09, 62.11, (Continued)

(56) References Cited

U.S. PATENT DOCUMENTS

| | | | |
|---|---|---|---|
| 3,549,036 A | 12/1970 | Ritsi | |
| 3,791,382 A * | 2/1974 | Collins | ........................ 128/853 |

(Continued)

OTHER PUBLICATIONS

Lee W. Young, International Search Report & Written Opinion issued in Application No. PCT/US2011/021306, dated Mar. 22, 2011, 6 pages.

*Primary Examiner* — Keri J Nelson
(74) *Attorney, Agent, or Firm* — Nicole M. Creegan (57) ABSTRACT

A surgical device comprising a first receptacle having a first mouth and a second receptacle having a second mouth, wherein the first mouth is in open communication with the second mouth via a joint joining the first receptacle with the second receptacle, and wherein the first mouth and second mouth open in a common direction. The surgical device can be used to effectively collect fluid during surgery in a first receptacle while simultaneously and independently retaining equipment and other medical supplies, such as tubes, wires, and/or tools, in a second receptacle. A drape sheet for covering at least a portion of a patient, the drape sheet optionally having a fenestration therein, with the surgical device being attached to the drape sheet.

27 Claims, 8 Drawing Sheets

(58) Field of Classification Search
USPC ...... 200/32.21; 206/144, 192–193, 195–196, 206/299, 349, 352, 363
See application file for complete search history.

(56) References Cited

U.S. PATENT DOCUMENTS

| | | | |
|---|---|---|---|
| 4,598,458 A | | 7/1986 | McAllester |
| 5,005,590 A | * | 4/1991 | Eldridge, Jr. .......... A61B 50/33 128/849 |
| 5,010,899 A | | 4/1991 | Thompson |
| 5,095,918 A | | 3/1992 | Busch |
| 5,143,091 A | | 9/1992 | Patnode et al. |
| 5,156,167 A | | 10/1992 | Busch |
| 5,339,831 A | | 8/1994 | Thompson |
| 5,779,366 A | | 7/1998 | McKenzie, III et al. |
| 6,032,670 A | | 3/2000 | Miller |
| 6,070,586 A | | 6/2000 | Harroll et al. |
| 6,298,855 B1 | | 10/2001 | Baird |
| 6,436,085 B1 | * | 8/2002 | Lauer ................... A61M 39/10 604/408 |
| RE38,485 E | | 4/2004 | Busch |
| 6,874,505 B1 | * | 4/2005 | Fenwick ............... A61B 19/08 128/849 |
| 7,556,429 B2 | | 7/2009 | Taheri |
| 2005/0061330 A1 | | 3/2005 | Fenwick et al. |
| 2006/0053523 A1 | * | 3/2006 | McNamara .................... 2/48 |
| 2008/0020143 A1 | * | 1/2008 | Moll ........................... 427/402 |

* cited by examiner

SURGICAL DEVICE HAVING MULTIPLE RECEPTACLES

CROSS-REFERENCE TO RELATED APPLICATIONS

This application claims priority to U.S. Provisional Application No. 61/295,531, which was filed on Jan. 15, 2010, the entirety of which is hereby incorporated by reference herein.

FIELD OF THE INVENTION

The present invention relates generally to surgical devices, and specifically to surgical pouches, for use during surgery. The present invention also relates to surgical drapes for use during surgery.

BACKGROUND OF THE INVENTION

Surgical drapes and surgical pouches are an important consideration in the medical field. It is well known to cover patients undergoing surgery with surgical drapes to create a sterile barrier around the surgical site. Some surgical drapes have fenestrations, or pre-defined openings, used during the procedures for one of two primary purposes, namely, to give access through the drape to the surgical site or to accommodate a portion of the patient's anatomy. In either case, the fenestration provides an opening in the drape to isolate the surgical site, and thereby create a sterile field between the body portion containing the surgical site and the remainder of the patient's body. It is also well know to use surgical pouches in combination with surgical drapes to collect fluids or retain limbs during surgeries.

During surgeries, surgeons need to control the placement of surgical equipment and supplies, such as tools, tubes, electrical wiring, and the like. Surgeons also need simple control of the fluid byproducts of surgery such as patient blood or fluids injected as part of the surgery, for example, irrigation fluids. Generally, simple surgical pouches have been used along with drapes to handle the fluid runoff while clamps and ties have been used for securing tubes and wires, for example, to a portion of the drape itself.

U.S. Pat. No. 5,339,831 discloses a pouch within a pouch design for collecting irrigation fluids and retaining a human appendage during surgery.

U.S. Pat. No. 6,874,505 discloses a single compartment pouch for retaining excess fluids, for securing surgical tubes and lines, and for storage of equipment.

SUMMARY OF THE INVENTION

There is an unmet need for a single device allowing surgeons to collect fluids in a first receptacle while retaining equipment, tools, wires, tubes or the like, in a second receptacle such that fluid is unlikely to interfere with the equipment, tools, wires, tubes, or the like, in the second receptacle.

The present invention provides for a surgical device comprising a first receptacle having a first mouth; and a second receptacle having a second mouth, wherein the first mouth is in open communication with the second mouth via a joint joining the first receptacle with the second receptacle, and wherein the first mouth and second mouth open in a common direction.

The present invention also provides for a surgical drape comprising a drape sheet for covering at least a portion of a patient, the drape sheet optionally having a fenestration therein; a surgical device attached to the drape sheet, the surgical device comprising a first receptacle having a first mouth; and a second receptacle having a second mouth, wherein the first mouth is in open communication with the second mouth via a joint joining the first receptacle with the second receptacle, and wherein the first mouth and second mouth open in a common direction.

The present invention also provides for a method of attaching the surgical device invention onto a surgical infection barrier product, such as, for example, a surgical drape.

The present invention also provides for a method of donning a surgical infection barrier product, such as, for example, a surgical drape, which also comprises the surgical device.

The above and still other advantages of the invention will be apparent from the detailed description and drawings. What follows are one or more preferred embodiments of the present invention.

DETAILED DESCRIPTION OF THE INVENTION

The present invention provides for a surgical device; a surgical infection barrier product having a surgical device; a method of attaching a surgical device to a surgical infection barrier product and a method of donning a surgical infection barrier product which comprises a surgical device. In a preferred embodiment of the present invention, the surgical infection barrier product comprises a surgical drape, optionally with fenestrations. The present invention provides for a surgical device comprising a first receptacle having a first mouth; and a second receptacle having a second mouth, wherein the first mouth is in open communication with the second mouth via a joint joining the first receptacle with the second receptacle, and wherein the first mouth and second mouth open in a common direction. The present invention can be used to effectively collect fluid during surgery in a first receptacle while simultaneously and independently retaining equipment and other medical supplies, such as tubes, wires, and/or tools, in a second receptacle.

The term "receptacle" refers to any shape or design capable of receiving an object. The term receptacle includes a container having a closed bottom, open or closed sides and an open or closed top. Receptacles include, but are not limited to pouches, bags, containers, sacks, chambers, and the like. In a preferred embodiment of the invention shown and described in detail herein, the surgical device comprises two receptacles, a first receptacle and a second receptacle. The first receptacle is configured to contain a volume of fluid while the second receptacle is configured to contain equipment, such as, but not limited to, tubes, wires, and/or tools. The surgical device of the present invention allows surgeries to be conducted in a controlled and sterile manner.

Figure 1:
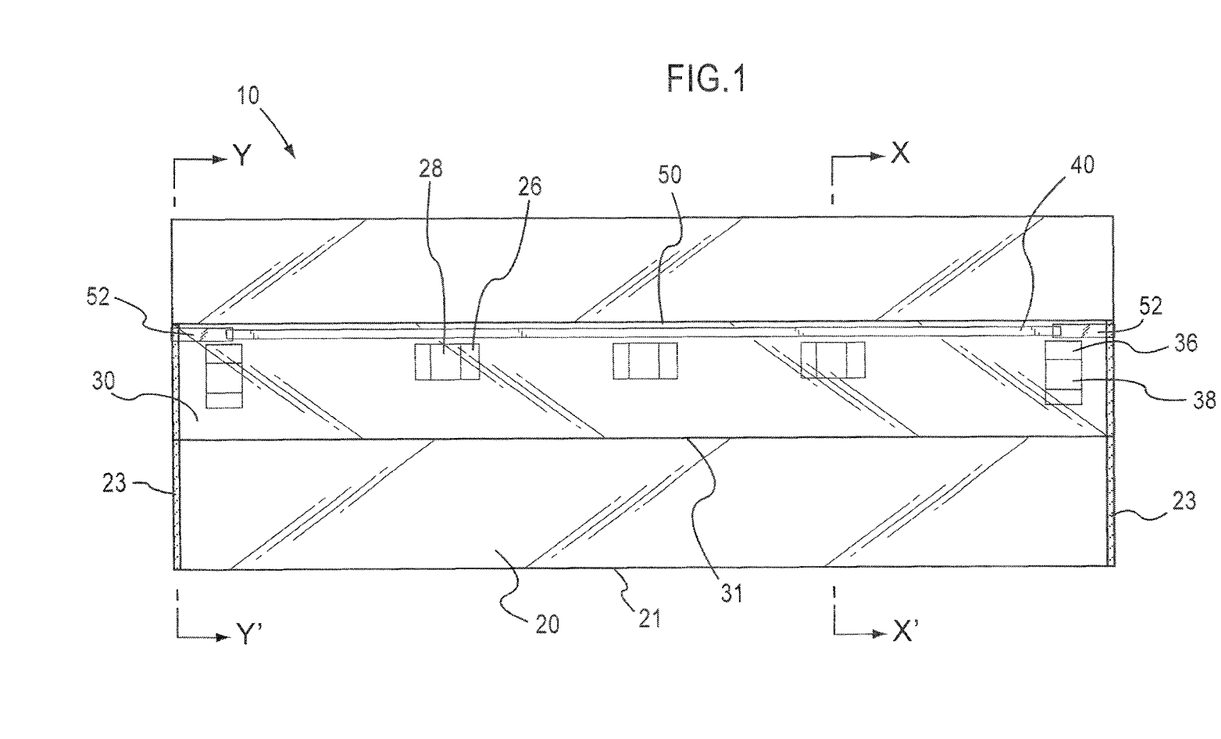
FIG. 1 is a front view of a surgical device.
Figure 2:
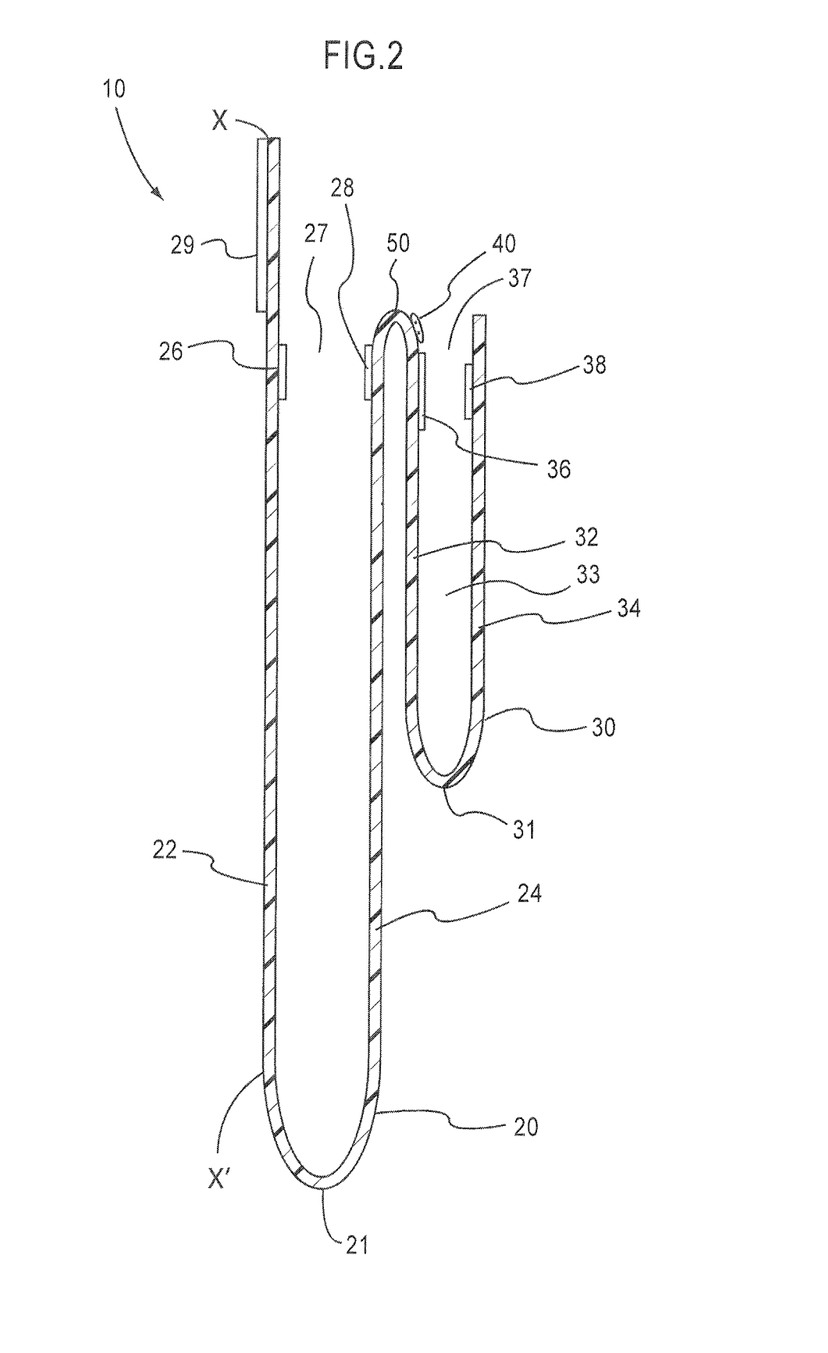
FIG. 2 is a sectional view taken along line X-X' of FIG. 1.

FIGS. 1 and 2 illustrate a preferred embodiment of the surgical device 10 for use during a surgical procedure. The surgical device 10 comprises a first receptacle 20 and a second receptacle 30. The first receptacle 20 comprises a first mouth 27 and the second receptacle 30 comprises a second mouth 37. As seen in FIG. 2, the first mouth 27 is in open communication with the second mouth 37 via a joint 50 that joins the first receptacle 20 to the second receptacle 30. Additionally, the first mouth 27 and the second mouth 37 open in a common direction. The joint 50 is disposed between the first receptacle 20 and the second receptacle 30.

FIG. 2 shows a sectional view of a preferred embodiment along line X-X' of FIG. 1. As seen in FIG. 2, a first panel 22 and a second panel 24 form the first receptacle. In a preferred embodiment, the first panel 22 and the second panel 24 extend substantially parallel to one another and are joined at a bottom point 21, thereby forming a closed end. The first panel and the second panel may be formed from two separate pieces of material joined together or may be formed from a single piece of material. At a point opposing the bottom point 21, the first panel 22 and the second panel 24 form the first mouth 27.

Similar to the configuration of the first receptacle 20, a third panel 32 and a fourth panel 34 form the second receptacle. In a preferred embodiment, the third panel 32 and fourth panel 34 extend substantially parallel to one another and are joined at a bottom point 31, thereby forming a closed end. The third panel and the fourth panel may be formed from two separate pieces of material joined together or may be formed from a single piece of material. At a point opposing the bottom point 31, the third panel 32 and the fourth panel 34 form the second mouth 37. It is also within the scope of the invention that any of the panels may extend at any angle so long as the first receptacle and second receptacle are capable of functioning as described herein.

Figure 3:
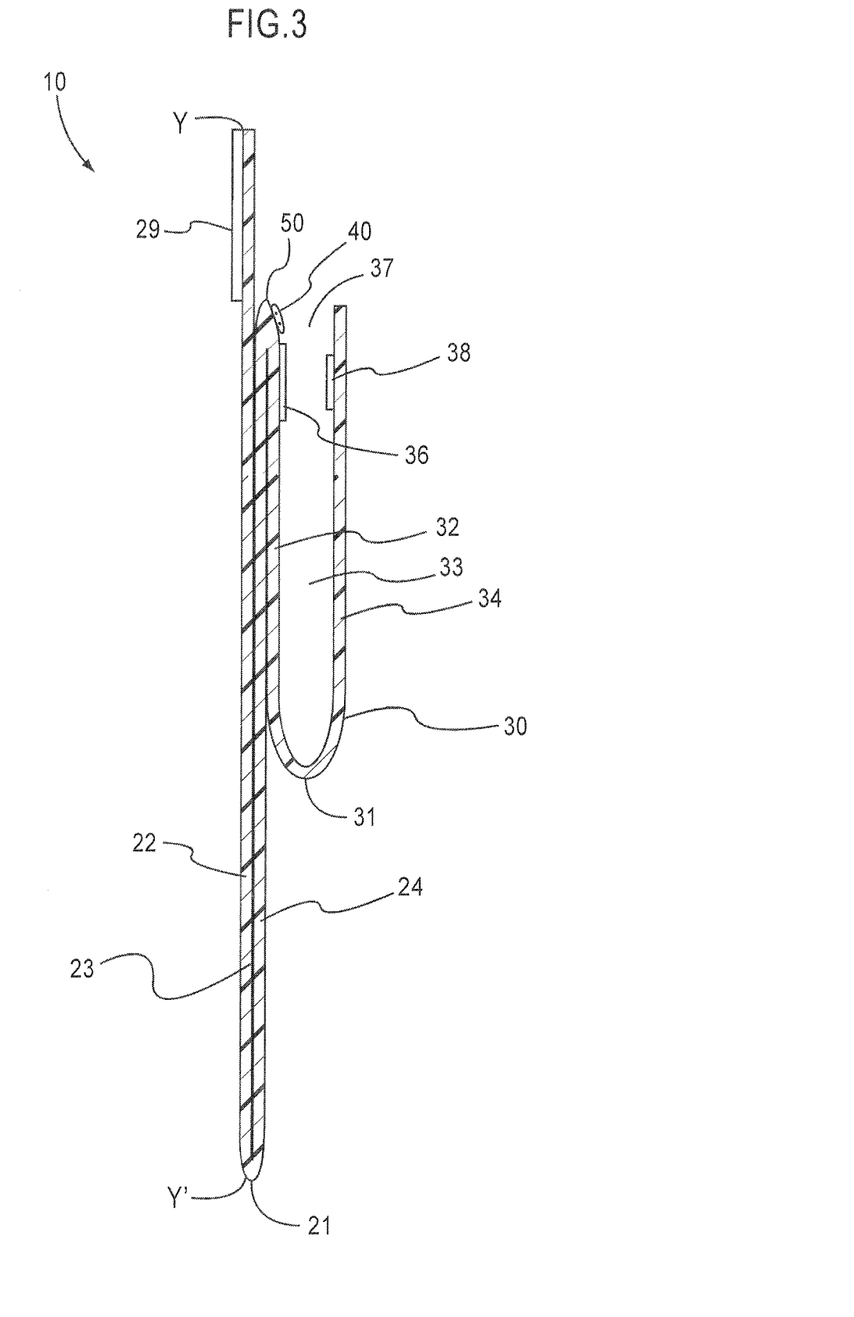
FIG. 3 is a sectional view taken along line Y-Y' of FIG. 1.
Figure 5:
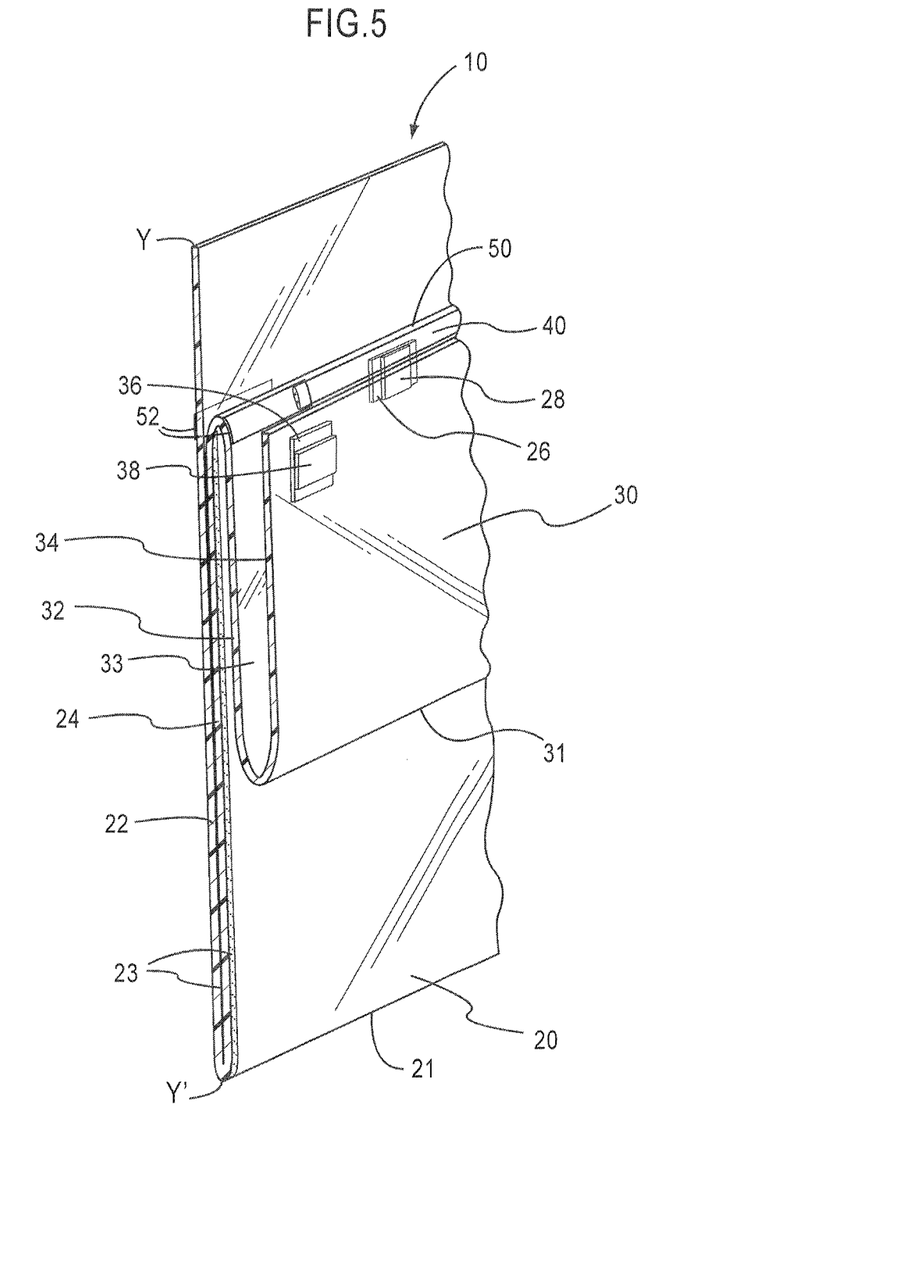
FIG. 5 is a partial perspective view taken along line Y-Y' of FIG. 1.

In a preferred embodiment, the first receptacle is configured to contain a volume of fluid and a second receptacle is configured to contain equipment. The first receptacle may have a greater volume than the second receptacle. As shown in FIG. 1, the sides of the first receptacle are sealed via a seal 23, thereby making the first receptacle 20 capable of containing a volume of fluid. As shown in FIGS. 3 and 5, the seal 23 is located along the sides of the first receptacle 20 and preferably extends from adjacent the bottom point 21 to the top of the second panel 24. Alternatively, the seal may extend from adjacent the bottom point 21 to any location along the first and second panels. It is within the scope of the invention that the seal be as wide as necessary to allow the first receptacle to contain a volume of fluid. For example the seal may be from ⅟16 inch to ⅜ inch, preferably, ⅟16, ⅛, ¼, or ⅜ inch wide. In a preferred embodiment, the seal 23 is a heat seal, but it is within the scope of the invention that any known method of creating a seal may be used, such as adhesive or hot wire sealing. Furthermore, the seal may be spaced from the periphery of the first receptacle.

Figure 6:
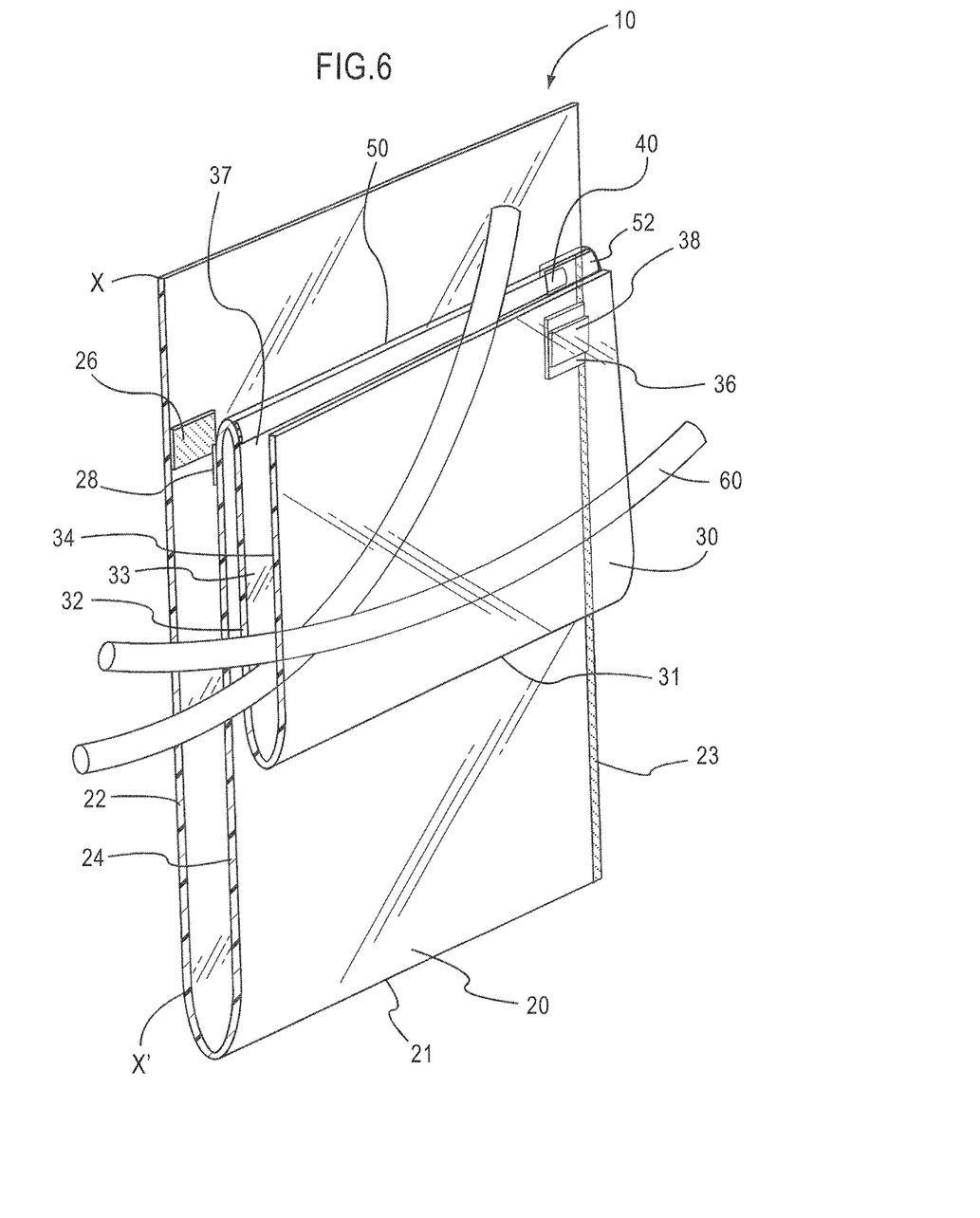
FIG. 6 is a perspective view taken along line X-X' of FIG. 1 additionally showing tubes located in a second receptacle.

In a preferred embodiment, the second receptacle 30 is not sealed along any sides. As shown in FIGS. 3 and 5, the second receptacle 30 is preferably open along at least a portion of each peripheral edge, thereby creating an open transverse channel 33. Thus, the second receptacle 30 is especially suited to retaining equipment, such as wires, tubes, and the like, that extend though the second receptacle via the channel 33. FIG. 6 shows tubes 60 extending through the channel 33, or through the second mouth 37.

As shown in FIG. 2, the surgical device 10 may further comprise a fastener 29, located on the outer surface of the first panel 22. The fastener 29 is preferably disposed on a portion of the outer surface of the first panel 22 above the first mouth 27, although the fastener may be positioned at any other position along the outer surface. Preferably, the fastener 29 extends ½ to 2 inches from the top of the surgical device X towards the first mouth 27. The fastener 29 allows the surgical device 10 to be attached to a surgical drape. In a preferred embodiment, the fastener 29 comprises adhesive and a releasable liner. Preferably, the fastener extends across the entire length of the first receptacle 20, but any length is sufficient as long as the fastener provides enough strength to hold the surgical device to the drape when in use. It is also within the scope of the invention that other known fasteners such as snap closures or hooks and loops may be used. The second panel is joined to the third panel via a joint. As shown in FIG. 2, when the surgical device is attached to a drape via the fastener 29, the second receptacle 30 is an outer receptacle and the first receptacle 20 is an inner receptacle. In this arrangement, the second panel 24 of the first receptacle 20 abuts against the third panel 32 of the second receptacle 30. Furthermore, as shown in FIG. 2, the joint 50 puts the first mouth 27 of the first receptacle 20 in open communication with the second mouth 37 of the second receptacle 30. Any flow of fluid that travels into the first receptacle 20 should not appreciably contact with the equipment located in the second receptacle 30, especially when the second mouth 37 is closed.

The surgical device may further comprise fasteners suitable for independently closing the first mouth and the second mouth. As shown in FIGS. 1 and 2, in a preferred embodiment, fasteners 26, 28 are disposed in at least two positions within the first receptacle 20, although placement outside receptacle 20 is also possible. In each pair of fasteners 26, 28 one fastener 26 is located on an inner face of the first panel 22 while the corresponding fastener 28 is located on the inner face of the second panel 24. When the fasteners 26, 28 mate, the first mouth 27 may be entirely or partially closed. Similarly, in a preferred embodiment, as shown in FIGS. 1 and 2, fasteners 36, 38 are disposed in at least two positions within the second receptacle 30, although placement outside the receptacle 30 is also possible. In each pair of fasteners 36, 38, one fastener is disposed on an inner face of the third panel 32 while the corresponding fastener 38 is located on the inner face of the fourth panel 34. When fastener 36, 38 mate, the second mouth 37 maybe be entirely or partially closed.

Figure 4:
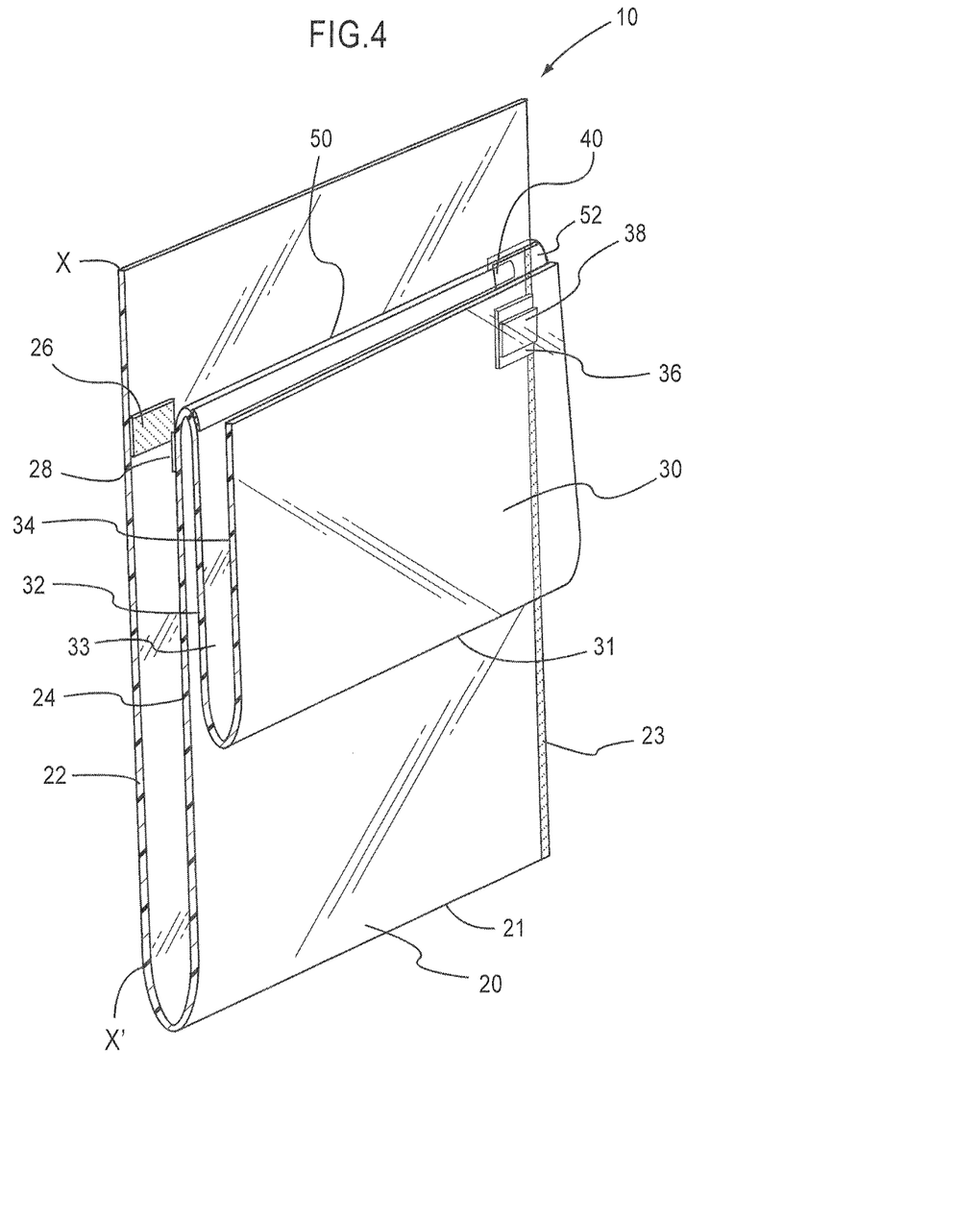
FIG. 4 is a perspective view taken along line X-X' of FIG. 1.

In a preferred embodiment, any or all of the fasteners are hook and loop fasteners because hook and loop fasteners enable adjustment of the first mouth 27 and second mouth 37 at any time. Furthermore, as shown in FIGS. 2 and 4, when the fastener 36 is relatively larger than the fastener 38, the size of the second receptacle 30 may be adjusted. Thus, the size and shape of the second receptacle may be optimized depending on the equipment held in the second receptacle 30. It is within the scope of the invention, however, that any suitable adjustable fasteners may be used such as adhesive, Velcro, or snap closures.

It is within the scope of the invention that any number of fasteners may be used. More fasteners may be desirable, for example, when the surgical device 10 must be capable of holding a large amount fluid and/or equipment. In a preferred embodiment the fasteners are able to support at least 10 pounds per square inch, such as from 10 to 18 pounds per square inch.

The surgical device may further comprise a shape retaining device that is configured to stabilize the first receptacle. In a preferred embodiment, as shown in FIG. 2, the retaining device 40 is disposed on the third panel 32 about the joint 50. As shown in FIG. 1, the retaining device 40 may be elongated and extend along the length of the third panel 32. The retaining device 40 is preferably malleable, and may comprise a least one bendable metal wire that is optionally coated. The coating may comprise polyethylene or other plastic. The retaining device 40 may be secured to the third panel 32 by double sided adhesive or any other suitable means.

Furthermore, the retaining device is preferably configured to prevent the fasteners from coming into contact with each other, thereby inadvertently closing the first mouth. It is within the scope of the invention that a retaining device may be added elsewhere on the surgical device wherever it is desired to maintain stabilization. Different shapes or orientations may also be used. For example, a retaining device may be segmented into multiple smaller devices. Furthermore, it is within the scope of the invention that any suitable material may be used so long as it is capable retaining the desired shape of the receptacle and may be used during surgery.

In a preferred embodiment of the surgical device, all four panels and the joint are formed of a single piece of material. When the surgical device is formed of a single piece of material, the first receptacle, the joint, and the second receptacle may be formed by folding the material in three places. Referring to FIG. 2, the first fold may occur at the bottom point 21 of the first receptacle 20, the second fold may occur at the joint 50, and the third fold may occur at the bottom point 31 of the second receptacle 30. It is within the scope of the invention, however, that any number of distinct pieces of material can be used to create the surgical device by joining them together. For example, in one embodiment, the first panel may be joined to the second panel, the third panel may be joined to the fourth panel 34, and the second panel may be joined to the third panel. In another embodiment, the first receptacle may be formed by a first piece of material and the second receptacle 30 may be formed by a second distinct piece of material, and the two receptacles may be joined together at the joint.

The first receptacle and the second receptacle may be made of any material suitable for use during surgeries and preferably are sterilizable and disposable. Preferably, the material is selected from nonwoven web materials which are gamma sterilizable. For example, polyethylene or polyester may be used. The nonwoven web materials may be wet laid, dry laid, spunlaced and spunbonded-melt blown-spunbonded (SMS) types well known to those skilled in this art. The material should be strong enough to support a volume of fluid in the first receptacle and equipment in the second receptacle. The material preferably waterproof. In an embodiment the material may comprise an antimicrobial agent, especially if being used around a point of incision. The material may also be antistatic. In a preferred embodiment, the material of the receptacles is transparent, such that fluid and/or equipment in the receptacles may seen by the naked eye. It is within the scope of the invention, however, that one of or both of the receptacles may be opaque to avoid light reflection during surgery.

The dimensions of the surgical device correlate to the particular surgery. In surgeries that require large incisions, involve a large amount of fluid, tools, tubes, and/or wires, then a larger surgical device is preferred. Likewise, a surgery requiring a small incision, involving small amount of fluid, few tools, tubes, and/or wires, then a smaller surgical device is preferred. Thus, it is within the scope of the invention that the surgical device may be any size.

The thickness of the material directly correlates to the amount of fluid and equipment the receptacles are able to hold. In one embodiment the thickness may be 3 millimeters to 5 millimeters. When the material is thicker, the receptacles are capable of retaining an open shape at the mouths. When the material is thinner it is more likely to collapse to a closed position. Furthermore, it is within the scope of the invention that an absorbent reinforcing material may be added to the surgical device 10 if desirable under particular surgical conditions.

FIG. 1 depicts the first receptacle 20 and the second receptacle 30 as elongated rectangles. It is within the scope of the invention, however, that the receptacles may be formed of any suitable shape so long as the first receptacle is capable of holding a volume of fluid and the second receptacle is capable of holding equipment. For example, while the first receptacle is illustrated as being substantially rectangular, it is within the scope of the invention that other geometries may be implemented depending on the circumstances in which the invention will be used. For instance, the first receptacle may have a conical or funnel shape having an open top that tapers to a bottom point. A suction tube or collection device may be connected to the bottom point of the receptacle to assist in removing or collecting fluid present in the receptacle.

Figure 7:
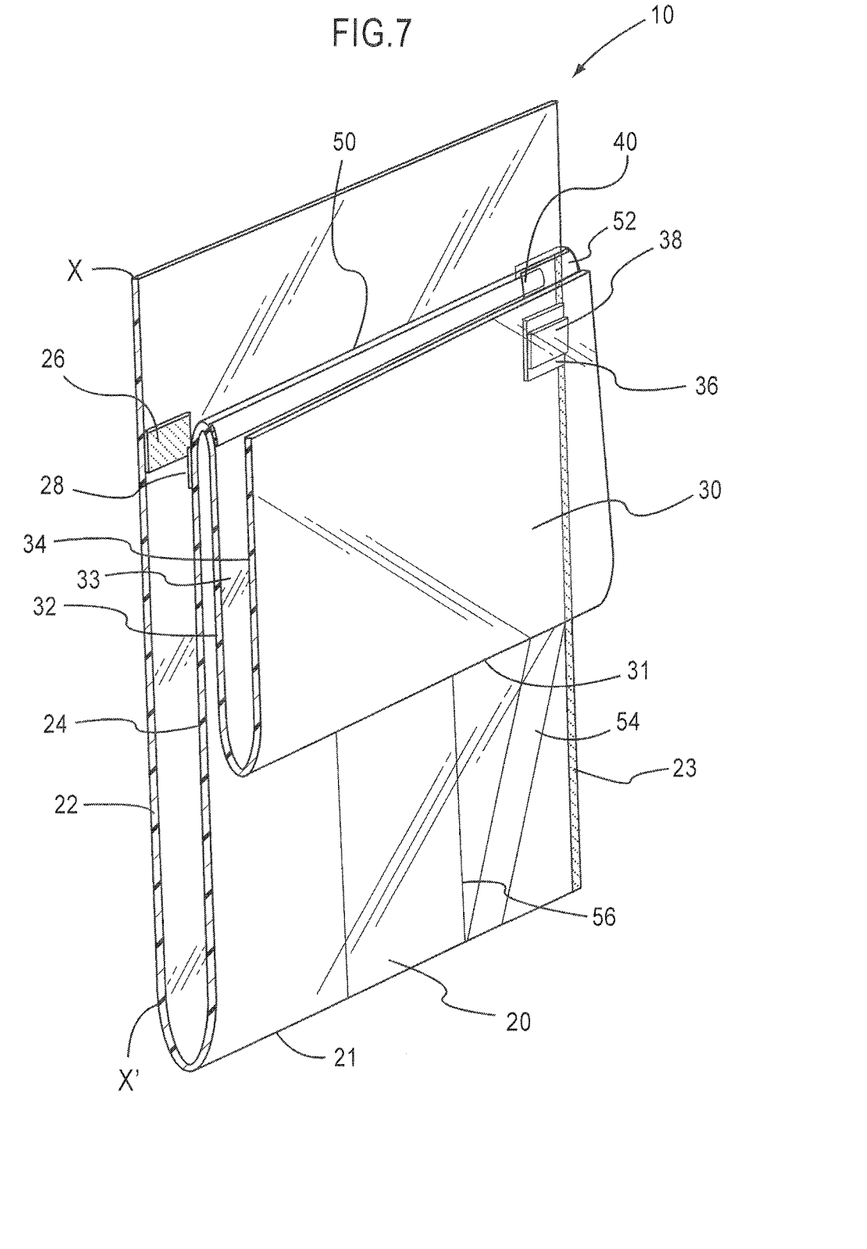
FIG. 7 is a perspective view taken along X-X' of FIG. 1 additionally showing compartments.

In another embodiment of the present invention, shown in FIG. 7, the first receptacle 20 may further comprise compartments 54. The compartments may be formed e.g. through heat seals 56. The heat seals may be disposed at varying intervals across the length of the receptacles to create small or large compartments. Furthermore, as shown in FIG. 7, the heat seals may be angled, thereby forming an angled compartment.

Although a preferred embodiment of the present invention has been described as comprising a first receptacle 20 and a second receptacle 30, it will be apparent to one of ordinary skill in the art, upon reading the description of the invention, that the surgical device 10 may comprise any number of additional receptacles (not shown). For instance, a third receptacle (not shown) might be provided either adjacent the first receptacle 20 (that is, on top of—or in front of—the first receptacle 20) or adjacent the second receptacle 30 (that is, below—or behind—the second receptacle 30) or both. This additional receptacle (not shown) may be used, for example, to provide additional compartments, pockets or the like, for the purpose of collecting surgical fluids or storing other surgical equipment, devices, products or supplies.

Figure 8:
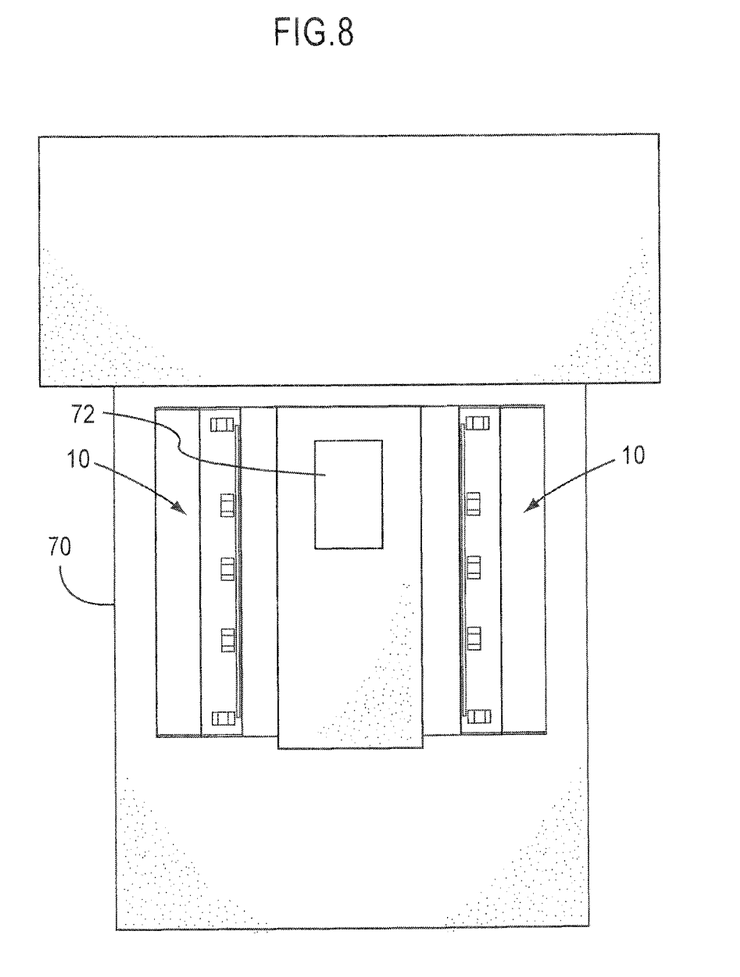
FIG. 8 is a front view of a surgical drape having the surgical device of FIG. 1 attached thereto.

As shown in FIG. 8, the present invention also includes a surgical drape 70 comprising a surgical device 10. The surgical drape 70 may have a fenestration 72 located around an operative site. The surgical drape is placed over at least a portion of the patient in use, so that the surgical site is accessible via the fenestration. The surgical device may be attached to the surgical drape via a fastener, as described above, or may be formed integrally therewith. The surgical device is capable of being attached to any existing surgical drape and in any desired position on the surgical drape.

Alternatively, a surgical device may also be pre-sealed to a surgical drape such that the surgical drape and the surgical device form a single unit.

The present invention also includes a method of attaching a surgical device to a surgical drape. The method comprises a step of attaching the surgical device to a surgical drape. The surgical device is typically positioned either adjacent the surgical site or flat across the patient.

The present invention also includes a method of donning a drape having a surgical device. The method comprises the step of donning a drape and the step of attaching a surgical device to the donned drape. The method also comprises a step of attaching a surgical device to a drape and the step of donning the drape having the surgical device already attached. Alternatively, if the drape and the surgical device are a single unit, the method comprises donning the surgical drape comprising the surgical device. The surgical device is placed on the surgical drape such that the surgical device is configured to collect fluid in the first receptacle during the surgery.

The general use of the surgical device will now be described. After donning the drape, with or without the surgical device already being secured to the surgical drape, the second receptacle may be utilized. Equipment needed during the operation may be contained within the second receptacle. For example, tubes for patient care and/or electrical wires necessary to run electrical equipment may pass through the channel of the second receptacle. If access to tools is necessary, the second receptacle also provides a convenient location to store them. During surgery, the surgical device, having been placed strategically to receive a volume of fluid, collects fluid in the first receptacle 20. The fluid may include bodily fluids originating from the patient, such as blood. The fluid may also include irrigation fluids used during the surgery. Because the first receptacle abuts the surgical drape, the fluids tend to collect in the first receptacle, with preferably no more than 10% of the fluid collecting in the second receptacle. Thus, the surgical device is capable of collecting fluid in the first receptacle while supporting equipment in the second receptacle, without a significant amount of fluid coming into contact with the equipment. During the operation a suction tube may also be inserted into the opening of the first receptacle to suction out fluid as it collects in the first receptacle. Alternatively, the first receptacle may be fitted with a drainage plug allowing the release of fluid from the first receptacle.

The invention has been described herein with reference to various specific and preferred materials, embodiments and techniques. It should be understood that many modifications and variations to such materials, embodiments and techniques will be apparent to those skilled in the art within the spirit and scope of the invention. Therefore, the invention should not be limited by the above description, and to ascertain the full scope of the invention, the following claims should be referenced.

All references cited herein are hereby incorporated by reference in their entirety.

The invention claimed is:

1. A surgical device comprising:
    a first panel, a second panel, a third panel, and a fourth panel, each panel having an inner surface and an outer surface, and each panel having a same transverse length as each other panel;
    a first receptacle having a first mouth, the first receptacle defined by the inner surface of the first panel and the inner surface of the second panel; and
    a second receptacle having a second mouth, the second receptacle defined by the inner surface of the third panel and the inner surface of the fourth panel;
    wherein the first mouth is in open communication with the second mouth via a joint joining the second panel with the third panel;
    wherein the outer surface of the third panel faces the outer surface of the second panel;
    wherein the first mouth and the second mouth open in a common direction;
    wherein the second receptacle comprises a transverse channel extending therethrough;
    wherein the first receptacle is configured to hold a volume of fluid;
    wherein the second receptacle is not sealed along any sides and configured to retain equipment in the channel;
    wherein the second receptacle is open along opposing peripheries of the second receptacle to allow the equipment to pass through the channel; and
    wherein the first receptacle, the second receptacle, and the joint comprise a single piece of material.

2. The surgical device of claim 1, wherein the first panel extends substantially parallel to the second panel and the third panel extends substantially parallel to the fourth panel.

3. The surgical device of claim 1, wherein the first receptacle has a greater volume than the second receptacle.

4. The surgical device of claim 1, wherein the first receptacle comprises a seal.

5. The surgical device of claim 4, wherein the seal is disposed along a periphery of the first receptacle.

6. The surgical device of claim 4, wherein the seal comprises a heat seal.

7. The surgical device of claim 1, wherein the joint is disposed between the first mouth and the second mouth.

8. The surgical device of claim 1, further comprising a fastener suitable for closing the first mouth and the second mouth.

9. The surgical device of claim 8, wherein the fastener comprises at least one of a hook and loop fastener, an adhesive, and/or a snap closure.

10. The surgical device of claim 8, wherein the fastener is adjustable.

11. The surgical device of claim 1, wherein an outer surface of the first receptacle comprises a fastener configured to attach the surgical device to a surgical drape.

12. The surgical device of claim 1, further comprising a retaining device attached to the second receptacle and extending substantially across the length of the second receptacle.

13. The surgical device of claim 12, wherein the retaining device is malleable and optionally coated.

14. The surgical device of claim 12, wherein an adhesive overlaps an end of the retaining device and extends to an outer surface of the first receptacle.

15. The surgical device of claim 1, wherein the surgical device comprises a waterproof, gamma sterilizable, nonwoven web material.

16. The surgical device of claim 15, wherein the material comprises polyethylene or polyester.

17. The surgical device of claim 15, wherein the material comprises spunlaced and spunbonded-melt blown-spunbonded (SMS).

18. The surgical device of claim 1, wherein the first receptacle and/or the second receptacle is transparent.

19. The surgical device of claim 1, wherein the first receptacle and/or the second receptacle is opaque.

20. The surgical device of claim 1, wherein the first receptacle comprises compartments.

21. The surgical device of claim 20, wherein the compartments are defined by heat seals.

22. The surgical device of claim 20, wherein the compartments are angled.

23. The surgical device of claim 1, wherein the first receptacle and the second receptacle are the only receptacles in the surgical device.

24. The surgical device of claim 1, further comprising a fastener suitable for closing one of the first mouth and the second mouth.

25. A surgical drape comprising:
   a surgical drape sheet for covering at least a portion of a patient, the surgical drape sheet having a fenestration; and
   the surgical device of claim 1.

26. A method of attaching a surgical device to a surgical drape comprising the step of attaching the surgical device of claim 1 to a surgical drape.

27. A method of donning a surgical drape comprising the steps of: laying
   a surgical drape over at least a portion of a patient; and attaching the surgical device of claim 1 to the surgical drape.

* * * * *